(12) United States Patent
Zak et al.

(10) Patent No.: US 7,953,609 B2
(45) Date of Patent: May 31, 2011

(54) DISEASE AND CASE MANAGEMENT SYSTEM

(76) Inventors: Solomon Zak, St Louis Park, MN (US); Rudra Duddala, Westboro, MA (US); Sashidar Kokku, Westboro, MA (US); Poladas James, Worcester, MA (US); Sireesha Parvatham, Westboro, MA (US); Parvathy Sashidhar, Westboro, MA (US)

(*) Notice: Subject to any disclaimer, the term of this patent is extended or adjusted under 35 U.S.C. 154(b) by 535 days.

(21) Appl. No.: 12/001,176

(22) Filed: Dec. 10, 2007

(65) Prior Publication Data
US 2009/0150182 A1    Jun. 11, 2009

(51) Int. Cl.
*G06Q 10/00* (2006.01)
*G06Q 50/00* (2006.01)
*G06Q 99/00* (2006.01)
*A61B 5/00* (2006.01)
*G06F 19/00* (2011.01)

(52) U.S. Cl. .............................. 705/2; 705/3
(58) Field of Classification Search .................. 705/2, 3
See application file for complete search history.

(56) References Cited

U.S. PATENT DOCUMENTS 6,802,810 B2 * 10/2004 Ciarniello et al. ............ 600/300
2005/0149869 A1 * 7/2005 Kehr et al. .................... 715/700

* cited by examiner

*Primary Examiner* — Gerald J. O'Connor
*Assistant Examiner* — Neha Patel
(74) *Attorney, Agent, or Firm* — Ashok Tankha; Lipton, Weinberger & Husick

(57) ABSTRACT

Disclosed herein is a computer implemented method and system that addresses the need for an online disease based and case based management of medical care. An online disease and case management system is provided. The information of the patients is retrieved from multiple information sources. The patient information is used to identify one of a disease condition in a patient population and a patient with a disease condition. Further, the patients are enrolled. The enrolled patients are educated about the disease condition for self monitoring of the disease condition. The status of the self monitored disease condition is recorded in a disease log. Visits to a provider are scheduled for medical treatment of the enrolled patients. The enrolled patients are monitored for medical progress based on the medical treatment provided. Further, the disease and case management of medical care are evaluated and reported based on clinical and financial outcomes.

18 Claims, 5 Drawing Sheets

DISEASE AND CASE MANAGEMENT SYSTEM

BACKGROUND

This invention, in general, relates to disease and case management. More particularly, this invention relates to an online disease based and case based management of medical care to a patient population.

The diseases prevailing in a population may be cured, controlled, and prevented through appropriate care and treatment. The population comprising unwell and healthy individuals need to be made aware of a particular disease, the associated comorbid conditions, the cure for the disease, and the prevention measures involved with the disease. For example, a disease such as polio, require an individual to immunize against the polio virus as a preventive measure. The population should be made aware of the knowledge about the treatment for polio, course of immunization for the disease, susceptible individuals and communities of the disease, and endemic or epidemic areas of the disease.

Further, certain chronic diseases, for example, diabetes mellitus, may be associated with one or more factors such as polycystic ovary syndrome, obesity, and family history. The diagnosis for chronic diseases requires specialized care and treatment to be given to the patient. The specialized care and treatment for the chronic diseases involves regular monitoring of the disease, diagnosis, and imparting knowledge about the disease and the treatment to the patient. The awareness of the disease and the subsequent monitoring and diagnosis of the disease may reduce health risks and associated health costs for the individual. The efficient implementation of a medical care program for providing disease awareness along with specialized care and treatment to a patient population requires the timely intervention and seamless integration of various personals including one or more of providers, specialists, disease managers, case managers, and health care organization. For streamlining the activities of the medical care program an online environment for managing and coordinating the various personals is required.

Hence, there is an unmet need for an online disease based and case based management of medical care to patients for streamlining the activities and seamless integration of the various personals of the disease and case based management.

SUMMARY OF THE INVENTION

The computer implemented method and system disclosed herein addresses the above stated need for an online disease based and case based management of medical care provided to patients.

In one embodiment of the computer implemented method and system disclosed herein, an online disease and case management system is used for disease based management of medical care to patients. The information of the patients is retrieved from multiple information sources using the online disease and case management system. The multiple information sources may be one or more of claims data, health risk questionnaires, and utilization analytics data. The retrieved information of the patients is used to identify a disease condition of the patient population. The step of identifying the disease condition of the patient population is performed utilizing at least one of diagnosis codes and service codes in a medical or pharmacy claim, lab and imaging values in the lab and imaging report, clinical values in an authorization request, information provided by the patients in a health risk questionnaire, and information provided by patients in a patient survey.

The method and system disclosed herein is used for enrolling the patients with identified disease condition for the disease based management of medical care. The step of enrolling the patients comprises inviting the patients for joining the disease based management of medical care utilizing one or more of electronic and non-electronic communication means. The identified patients may accept or decline the invitation offer to join the disease based management of medical care. The enrolled patients are educated about the disease condition for self monitoring of the disease condition. The status of the self monitored disease condition is recorded in a disease log of personal health record on the online disease and case management system by the patients.

The method and system disclosed herein further includes scheduling visit to a provider for medical treatment of the enrolled patients based on the recorded status. A disease manager manages the enrolled patients and educates the enrolled patients about the disease condition. Further, the enrolled patients are monitored for medical progress based on the medical treatment. The method and system disclosed herein generates multiple reports on the online disease and case management system. The generated reports are further used for rewarding the provider and the enrolled patients.

In one embodiment of the computer implemented method and system disclosed herein, the online disease and case management system is used for case based management of medical care to a patient. The information of the patient is retrieved from multiple information sources using the online disease and case management system. The retrieved information of the patient is used to identify a patient with a disease condition. The method and system disclosed herein enrolls the identified patient for the case based management of medical care. The enrolled patient is managed by a case manager. The case manager provides personalized support to the enrolled patient. The enrolled patient is educated about the disease condition for self monitoring of the disease condition. The status of the self monitored disease condition is recorded in a disease log of personal health record on the online disease and case management system by the patient. The method and system disclosed herein further includes scheduling visits to a provider for medical treatment of the enrolled patient based on the recorded status. Further, the enrolled patient is monitored for medical progress based on the medical treatment.

The objective of disease based management of medical care include coordination of care and providing a liaison between the patients, the provider, and one of the disease manager and a case manager to improve the medical status of the patients.

BRIEF DESCRIPTION OF THE DRAWINGS

The foregoing summary, as well as the following detailed description of the embodiments, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
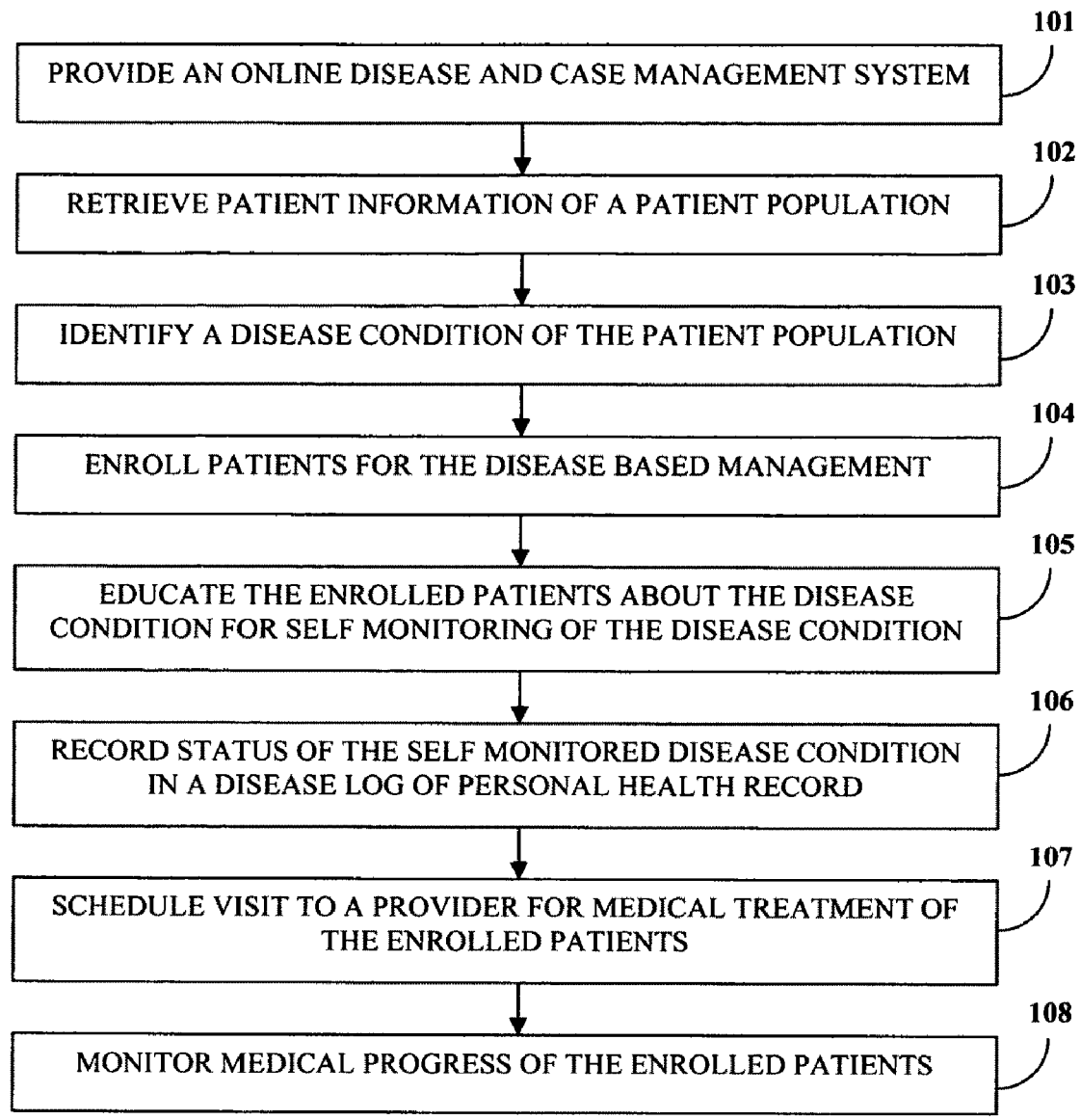
FIG. 1 illustrates a computer implemented method of disease based management of medical care provided to a patient population.

FIG. 1 illustrates a method of disease based management of medical care provided to a patient population. The disease based management of medical care is used for identifying one or more of diseases and disease conditions of a patient population and managing the patient population having the identified diseases and disease conditions. The patient population having the identified diseases and disease conditions are managed by a disease manager. The disease manager educates and manages the patient population about the disease and disease conditions. The computer implemented method disclosed herein provides 101 an online disease and case management system 300 for disease based management of medical care. The information of patients of a patient population is retrieved 102 from multiple information sources using the online disease and case management system 300. The retrieved information is stored in a retrieved patient queue 303a of a patient information database 303. The multiple information sources may be one or more of claims data, health risk questionnaires, and utilization analytics data.

Further, the retrieved information of the patients is used to identify 103 a disease condition of the patient population. The step of identifying the disease condition of the patient population is performed utilizing at least one of diagnosis codes and service codes in a medical or pharmacy claim, lab and imaging values in the lab and imaging report, clinical values in a authorization request, information provided by the patients in a health risk questionnaire, and information provided by patients in a patient survey. The disease condition may be monitored and managed based on an international classification of diseases (ICD) codes, disease parameter and disease parameter values, age, and gender of the patients. The identified patient information is stored in an identified disease patient queue 303b of the patient information database 303.

The computer implemented method disclosed herein enrolls 104 the patients for the disease based management of medical care. The step of enrolling the patients comprises inviting the patients for joining the disease based management of medical care utilizing one or more of electronic and non electronic communication means. The patients may accept or decline the invitation offer to join the disease based management of medical care. The enrolled patients are provided with a user name and password for using the online disease and case management system 300. Further, the enrolled patients provide the date of birth for authenticating and accessing the online disease and case management system 300. The enrolled patients are educated 105 about the disease condition for self monitoring of the disease condition. The step of educating the enrolled patients includes providing one or more of disease information material, instructions to the enrolled patients on general and specific medical care, and responses to queries of the enrolled patients using the online disease and case management system 300.

The status of the self monitored disease condition of the enrolled patients is recorded 106 in a disease log of personal health record on the online disease and case management system 300 by the enrolled patients. The recorded status of the enrolled patients is used to determine medical status of the enrolled patients. The medical status of the enrolled patients may be changed to one of acute medical status and normal medical status based on the recorded status. The method disclosed herein further includes scheduling 107 a visit to a provider for medical treatment of the enrolled patients based on the recorded status. The schedules of the enrolled patients are synchronized with schedules of one or more of the disease manager and the provider using the online disease and case management system 300. The disease manager provides online disease based management support to the enrolled patients. The disease manager further supervises and manages a patient medical diary using the online disease and case management system 300.

The enrolled patients are monitored 108 for medical progress based on the medical treatment provided. The step of monitoring medical progress is performed utilizing one or more of laboratory results and clinical values of the enrolled patients. The disease manager may also define and monitor alerts for one or more of the patient, the provider, the disease manager, a case manager, and a medical director. The method disclosed herein generates a plurality of reports on the online disease and case management system 300. The generated reports comprise utilization metrics of the disease based management of medical care. The utilization metrics are used for rewarding the provider, the disease manager, and the enrolled patients.

Further, the step of generating reports for the disease managers, disease management supervisor, and the provider comprises calculating a success rate, wherein the success rate is calculated from a plurality of performance indices. The success rate of disease manager's performance is based on the ratio of number of patients enrolled by the disease manager to the number of patients assigned for enrollment, the ratio of the number of patients with normal medical status to the total number of patients managed by the disease manager, and the number of catastrophic patients. Patients are classified as catastrophic patients when the medical expenses exceed a predefined value. For example, patients with medical expenses more than $20,000 may be considered as catastrophic patients. The performance of the disease management supervisor is an aggregate of the performance of all the disease managers assigned to the disease management supervisor. The generated reports are used to rate the provider based on one or more of utilization cost performance, referrals, quality of care, and the number of catastrophic cases. The effectiveness of participation of the enrolled patients in the disease management of the medical care are determined and rated based on the reports. Further the provider ratings and the patient ratings are used for rewarding the provider and the enrolled patients, respectively.

Figure 2:
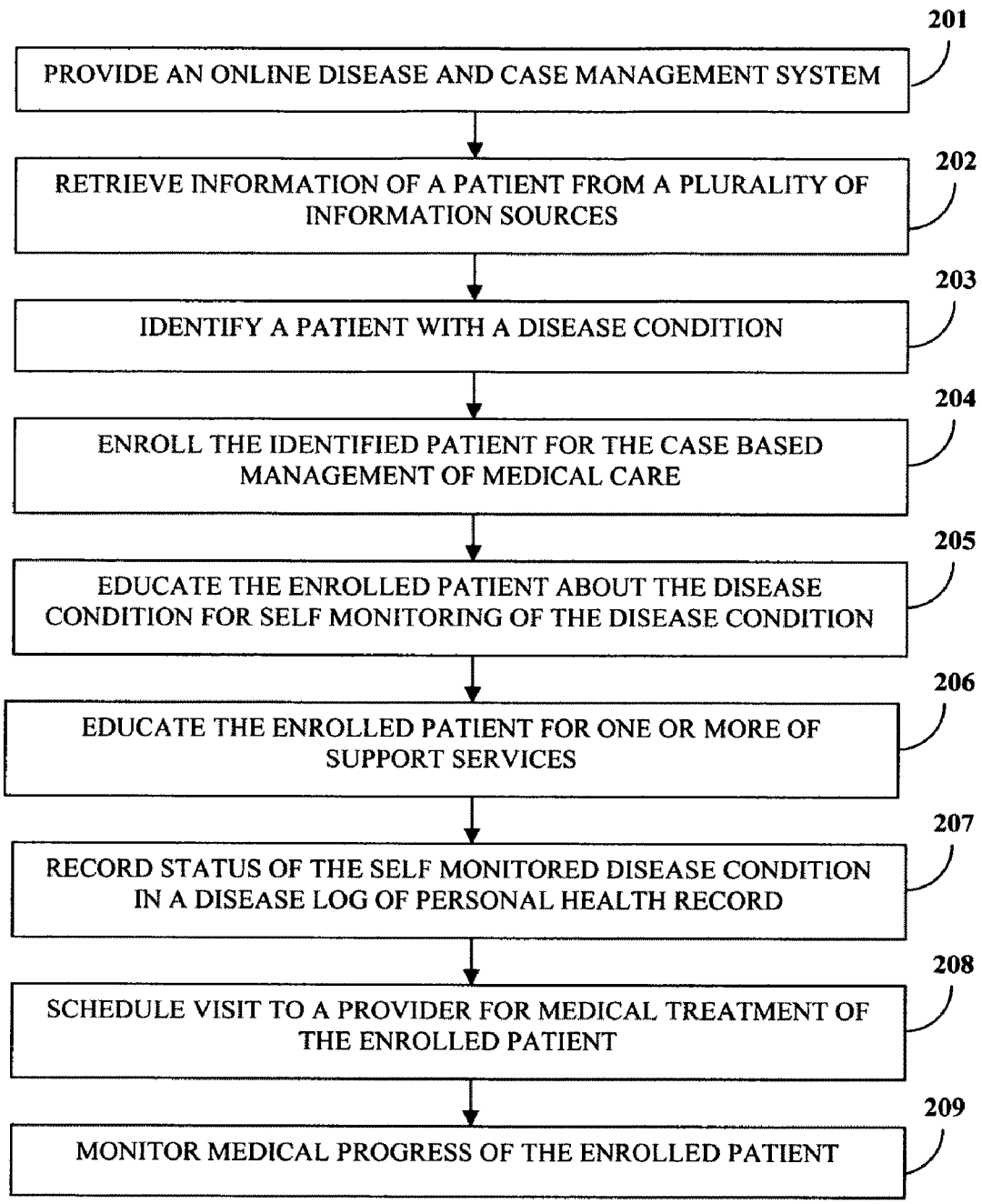
FIG. 2 illustrates a computer implemented method of case based management of medical care provided to a patient.

FIG. 2 illustrates a method of case based management of medical care provided to a patient. The computer implemented method disclosed herein provides 201 an online disease and case management system 300 for disease and case based management of medical care. The information of a patient is retrieved 202 from multiple information sources using the online disease and case management system 300. The retrieved information of the patient is used to identify 203 a patient with a disease condition. The method disclosed herein enrolls 204 the identified patient for the disease and case based management of medical care. The enrolled patient is managed by a disease manager and a case manager. The case manager provides personalized support to the enrolled patient.

The enrolled patient is educated 205 about the disease condition for self monitoring of the disease condition. Further, the enrolled patient is educated 206 for one or more of support services comprising community programs related to the disease condition, coordination between providers of medical care, transport services, and financial counseling. The status of the self monitored disease condition is recorded 207 in a disease log of the personal health record on the online disease and case management system 300 by the patient. The method disclosed herein further includes scheduling 208 the patient's visits to a provider for medical treatment of the enrolled patient based on the recorded status. Further, the enrolled patient is monitored 209 for medical progress based on the medical treatment.

Figure 3:
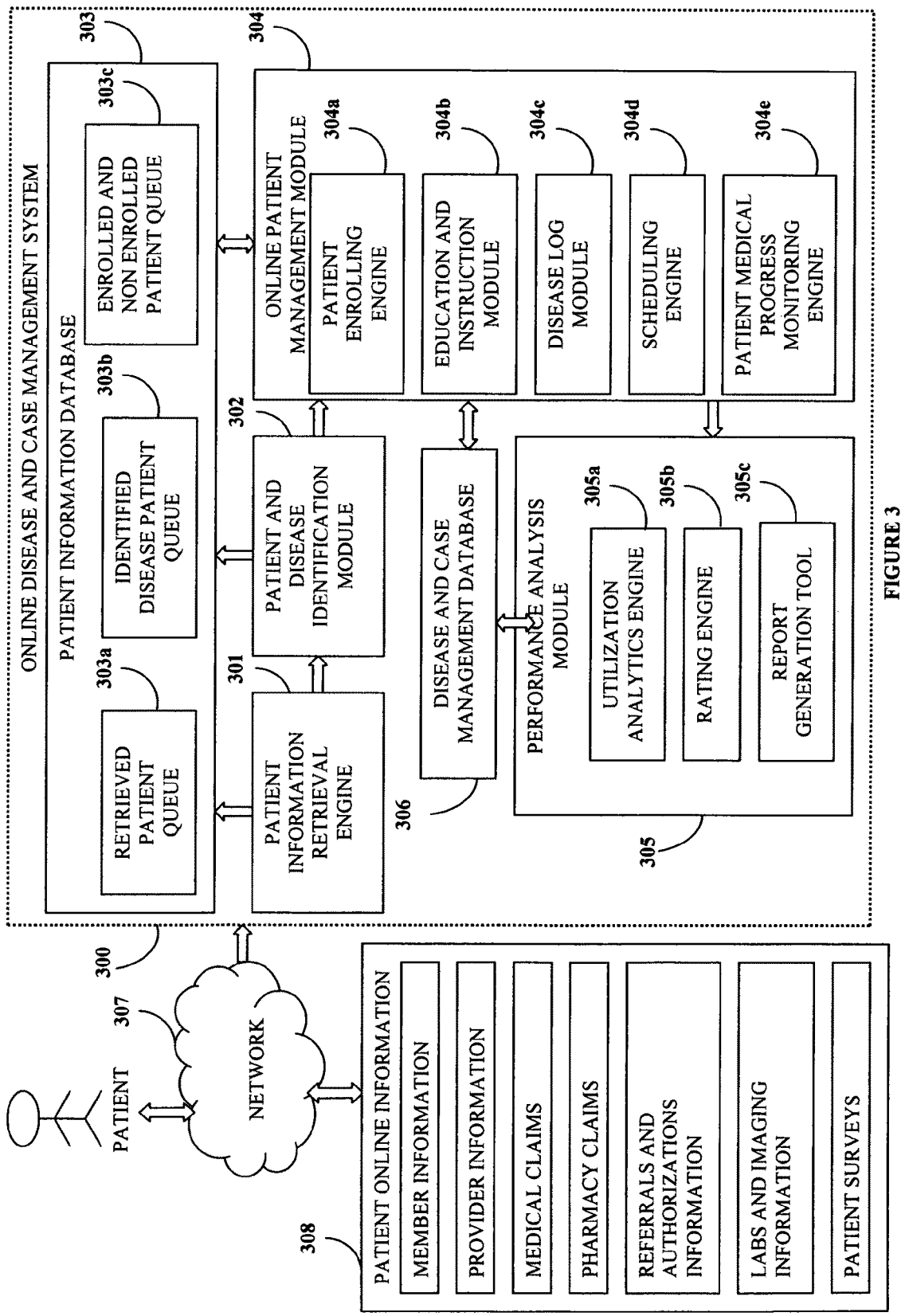
FIG. 3 illustrates a computer implemented system for disease based and case based management of medical care provided to patients.

FIG. 3 illustrates a system for disease based management of medical care provided to patients. The system disclosed herein comprises an online disease and case management system 300, an online patient management module 304, a patient information retrieval engine 301, a patient and disease identification module 302, a performance analysis module 305, a patient information database 303, and a disease and case management database 306. The online disease and case management system 300 is used for providing the disease based and case based management of medical care to the patients. Multiple diseases and disease parameters are configured using the online disease and case management system 300. Further, the online disease and case management system 300 may be accessed any time by patients, providers, disease managers, case managers, medical directors, and disease management supervisors.

The online disease and case management system 300 may be integrated with medical management systems including utilization analytics system, healthcare effectiveness data and information set (HEDIS) system, and authorization management system, health risk questionnaire system, lab and imaging database and patient surveys. The online patient management module 304 further comprises a patient enrolling engine 304a, an education and instruction module 304b, a disease log module 304c, a scheduling engine 304d, and a patient medical progress monitoring engine 304e. The patient information database 303 further comprises a retrieved patient queue 303a, an identified disease patient queue 303b, and an enrolled and non enrolled patient queue 303c. The performance analysis module 305 further comprises a utilization analytics engine 305a, a rating engine 305b, and a report generation tool 305c.

The patient information retrieval engine 301 is used for retrieving a plurality of online patient information 308. The online patient information 308 includes member information, provider information, medical claims, pharmacy claims, referrals and authorizations information, information from labs and images, and patient surveys. The information is retrieved from the plurality of information sources via a network 307. The plurality of information sources may be one or more of claims data, health risk questionnaires, and utilization analytics data. The patient and disease identification module 302 is used for identifying one of the disease conditions in a patient population and the patients with a disease condition. The disease condition may be monitored and managed based on ICD codes, disease parameter and parameter values, age, and gender of the patient.

The online patient management module 304 is used for coordinating the disease based and case based management of medical care. The patient enrolling engine 304a of the online patient management module 304 is used for enrolling the patients for the disease based and case based management of medical care. The enrolling engine 304a sends an invitation to the patients for joining the disease based and case based management of medical care based on the availability of an email identity of the patients. If the identified patients possess an e-mail identity, the enrolling engine sends the invitation through an electronic mail to the patients. If the patients do not possess an e-mail identity, the enrolling engine sends the invitation via automated phone messaging or mail to the patients. The description on the method of enrolling is described in the detailed description of FIG. 4. The education and instruction module 304b is used for providing information on self monitoring of a disease condition to the patients.

The disease log module 304c is used for recording status of the self monitored disease condition by the patients. The self monitored disease condition may be recorded from the residence by the patients. The scheduling engine 304d is used for scheduling a visit to a provider for medical treatment of the enrolled patients based on the recorded status. Further, the scheduling engine 304d synchronizes the online scheduler of the enrolled patients with the online scheduler of the provider and a disease manager. The patient medical progress monitoring engine 304e is used for monitoring medical progress of the enrolled patients based on the medical treatment. The patient medical progress monitoring engine 304e uses the recorded status in the disease log module 304c to determine the medical status of the enrolled patients. The medical status of the enrolled patients may be one of acute medical status and normal medical status. The disease and case management database 306 is used for storing one or more of list of diseases, international classification of diseases (ICD) diagnosis code, current procedure terminology (CPT) code, national drug classification (NDC) code for each disease, the clinical parameter and parameter values for each disease, education and instruction information, recorded status, patient schedules, and medical progress of the enrolled patients.

The performance analysis module 305 is used for analyzing the performance of one of the provider, the disease manager, the case manager, and the disease based and case based management of medical care of the patients. The utilization analytics engine 305a is used for performing the utilization analysis of the disease based and case based management of medical care of the patients. The rating engine 305b is used for ranking the provider based on performance. The report generation tool 305c is used for generating a plurality of reports on the online disease and case management system 300. The patient information database 303 is used for storing information on one or more of retrieved patient information, identified patient information, enrolled patient information, and non enrolled patient information. The retrieved patient information is stored in the retrieved patient queue 303a. The identified patient information is stored in an identified disease patient queue 303b. The information on the enrolled patient and non-enrolled patient is stored in the enrolled and non-enrolled patient queue 303c.

Figure 4:
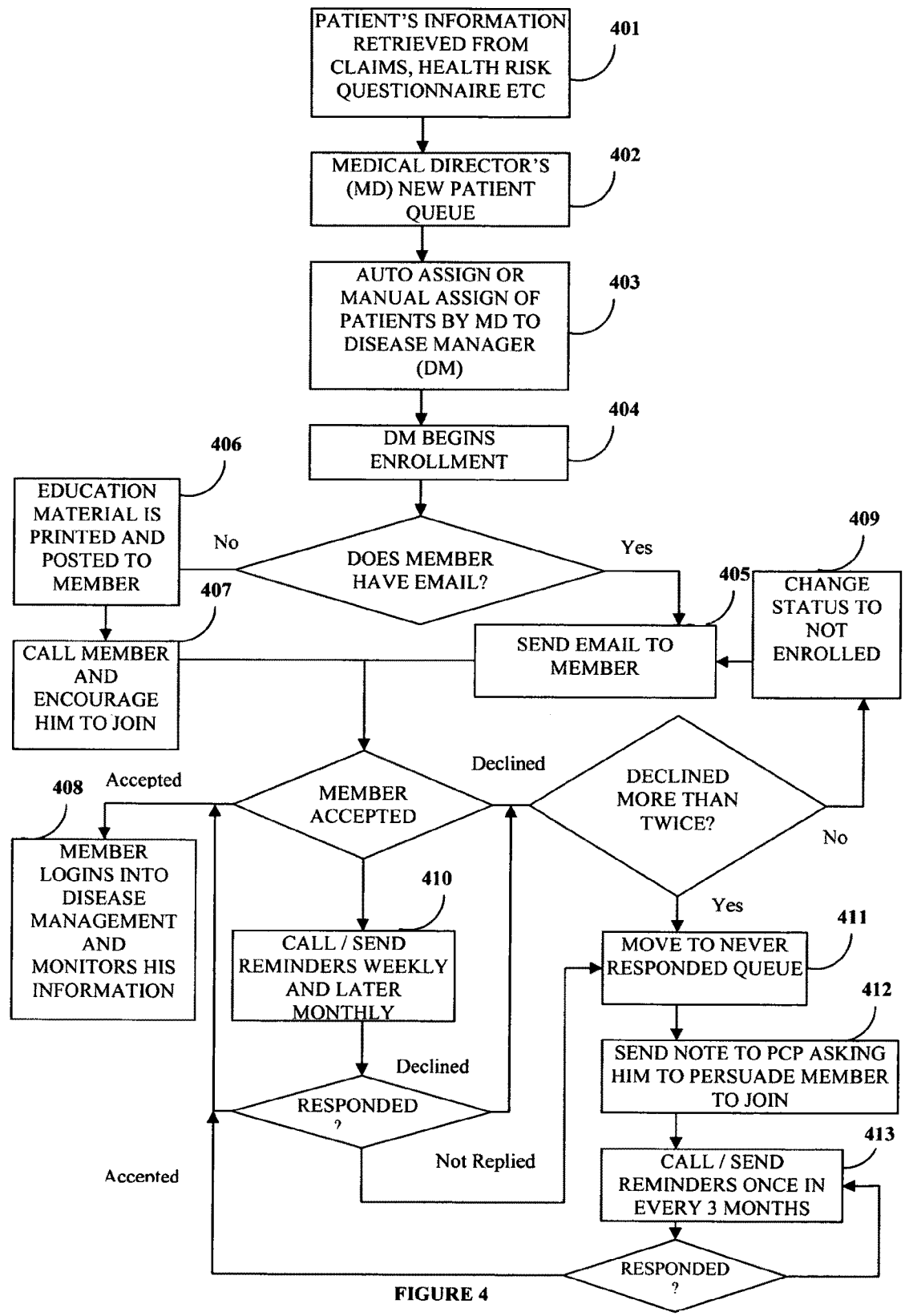
FIG. 4 illustrates an enrollment flow chart for disease based management of medical care.

FIG. 4 illustrates an enrollment flow chart for disease based management of medical care. The information of a new patient may be retrieved 401 from claims data, health risk questionnaires, and utilization analytics data. The information of the new patient in the disease management program is stored in the retrieved patient queue 303a of the online disease and case management system 300. The information of the new patient stored in the retrieved patient queue 303a is accessed 402 by a medical director (MD). The new patient is assigned 403 a disease manager (DM) by the medical director (MD) manually or automatically using the online disease and case management system 300. The disease manager (DM) enrolls 404 the patient for the disease management program. The step of enrollment comprises inviting the patient to join the disease management program. If the patient has an electronic mail identity, the patient is sent 405 an electronic mail and is given a username and password.

The patient receives information about the disease management program. Further, the patient is asked to join in the disease management program by logging in to the online disease and case management system 300 using the username and password. If the patient does not have the electronic mail identity, education material and further information about the disease management program is sent 406 to the patient through mail. The DM may call the patient and encourage 407 the patient for joining the disease management program. If the patient logs in and accepts the invitation, the patient can access 408 the disease management information and monitor the disease.

Further, for accessing the online disease and case management system 300, the patient may authenticate by entering the date of birth. The patient may be monitored by the disease manager, the provider, and the patient himself. If the patient declines to join, the patient's status is changed 409 to "not enrolled". The DM may further send a second invitation for enrollment. If the patient doesn't respond to the invitation, a reminder may be sent 410 weekly and monthly asking the patient to join the disease management program. If the patient declines the invitation for example, more than twice, the patient may be moved 411 to a never responded queue. The primary care physician (PCP) of the patient is notified by the online disease and case management system 300 to persuade 412 the patient to join the disease management program. Further, the patient is sent 413 reminders periodically, for example, once in three months, to join the disease based management of medical care.

Figure 5:
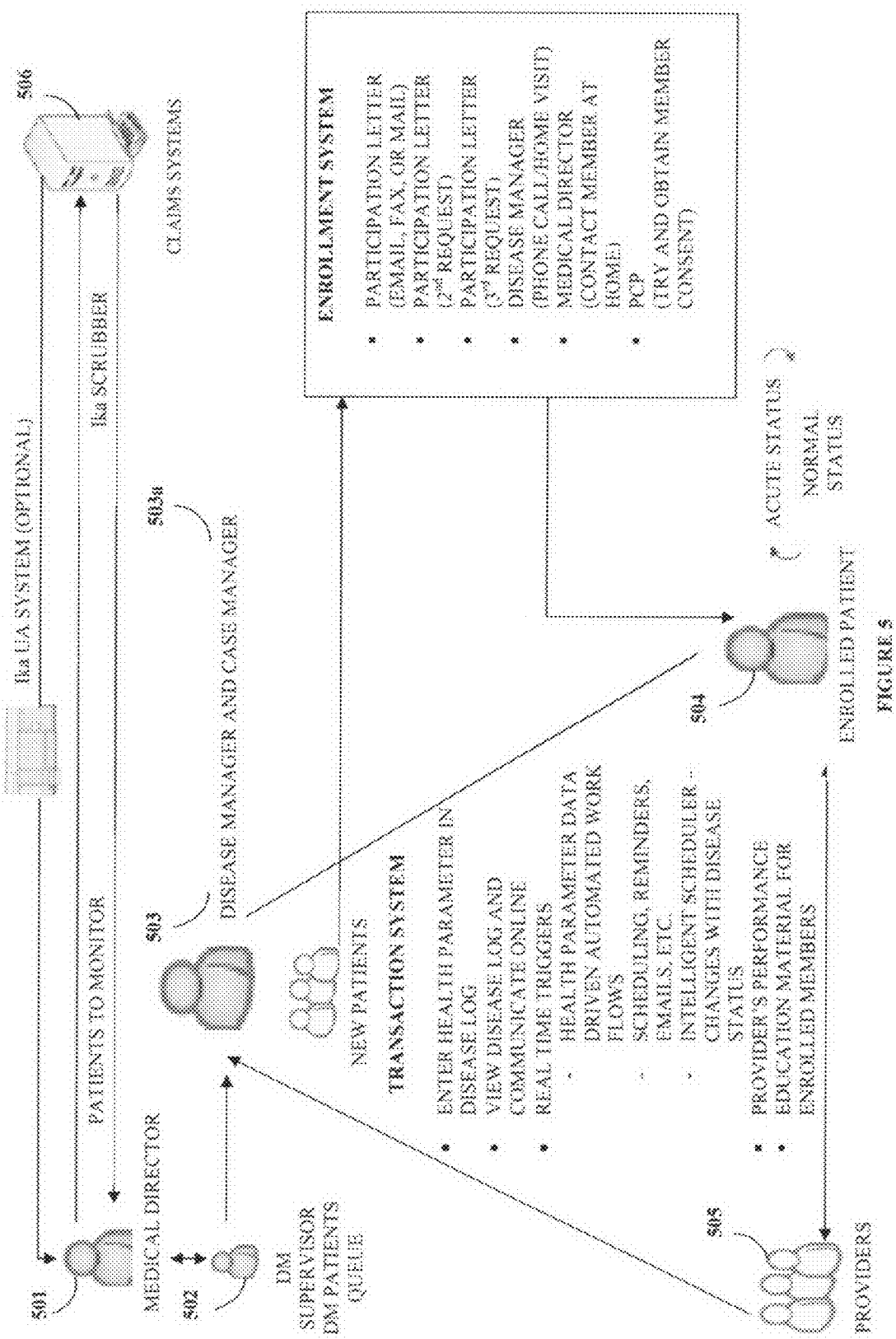
FIG. 5 exemplarily illustrates work flow of the online disease and case management system.

FIG. 5 exemplarily illustrates work flow of an online disease and case management system 300. The medical director 501 retrieves patient information from the claims processing system 506. The patient information may also be retrieved from a utilization analytics system. The medical director 501 utilizes a "scrubber" in the online disease and case management system 300 to automatically filter in "high cost" and "high clinical risk" patients using financial and clinical filters. Further, the medical director 501 may configure diseases and associated parameters in a disease management program. The medical director 501 may configure the diseases and associated parameters by adding new diseases, adding new parameters, and changing values for each associated parameters of a disease, by using the online disease and case management system 300.

The "high cost" and "high clinical risk" patients are forwarded by the medical director 501 to the disease management supervisor 502. The disease management supervisor 502 assigns patients to disease manager 503 or case manager 503*a* for enrolling new patients.

The information of the identified patient is stored in a queue 303*a*. The queue 303*a* is maintained by a disease management supervisor 502 who acts as a mid level authority between the medical director 501 and one of the disease manager 503 and the case manager 503*a*. The disease manager 503 enrolls the patient for the disease management program. The step of enrolling for the disease based management includes the step of sending a participation request letter to the identified patient. The participation request letter comprises an invitation for inviting the identified patient to join for the disease management program. The participation letter may be sent to the identified patient utilizing one or more of electronic and non electronic communication means. If required, the participation letter may be sent to the identified patient more than one time.

The identified patient may further enroll for a case management program by agreeing and accepting a patient consent letter sent by the medical director 501. The patient consent letter may include a non disclosure agreement of the patient information between the patient and the medical director 501. The enrolled patient 504 is assigned a case manager 503*a*. The case manager 503*a* assists the enrolled patient 504 for receiving the appropriate care. Further, the case manager 503*a* may send a welcome letter to the enrolled patient 504. The welcome letter comprises a welcome note by the case manager 503*a* to the enrolled patient 504. The case management program may be provided at no additional cost for the enrolled patient 504. The enrolled patient 504 for the case management program is provided with medical information and advice regarding the disease condition. The case manager 503*a* works in conjunction with enrolled patient's 504 physician's orders, locates appropriate provider 505 of care and services, assists with solutions to provider 505 service problems, and coordinates care with multiple providers 505. Further, the medical director 501 may send a notification letter to a physician associated with the enrolled patient 504 for notifying the enrollment of the patient.

Further, the enrolled patient 504 is educated about the disease condition for self monitoring of the disease condition. The step of educating the enrolled patient 504 includes one or more of providing disease information material, instructing the enrolled patient 504, and responding to patient queries using the online disease and case management system 300. The status of the self monitored disease condition of the enrolled patient 504 is recorded in a disease log of personal health record on the online disease and case management system 300 by the enrolled patient 504. The recorded status of the enrolled patient 504 is used to determine medical status of the enrolled patient 504. The medical status may be one of acute medical status and normal medical status. The disease manager 503 schedules visits of the enrolled patient 504 to the provider 505 for medical treatment of the enrolled patient 504 based on the recorded status. The enrolled patient 504 is monitored for medical progress based on the medical treatment provided. The step of monitoring medical progress is performed systematically utilizing one or more of laboratory results and clinical values of the enrolled patient 504. The disease manager 503 may also define and monitor alerts for at least one of the patient, the provider 505, the disease manager 503, the case manager 503*a*, and the medical director 501.

The case manager 503*a* may send the enrolled patient 504 a closing letter. The closing letter may comprise the reasons for stopping the case management services offered by the case manager 503*a*. The reasons may be at least one of improved medical status of the enrolled patient 504, exhausted benefits, ineligible benefits, or the enrolled patients' 504 decision to opt out of the case management program. Further, a case management survey form is provided to the enrolled patient 504 for commenting on the services provided and benefits gained during the period of enrollment.

It will be readily apparent that the various methods and algorithms described herein may be implemented in a computer readable medium appropriately programmed for general purpose computers and computing devices. Typically a processor, for e.g., one or more microprocessors will receive instructions from a memory or like device, and execute those instructions, thereby performing one or more processes defined by those instructions. Further, programs that implement such methods and algorithms may be stored and transmitted using a variety of media, for e.g., computer readable media in a number of manners. In one embodiment, hard-wired circuitry or custom hardware may be used in place of, or in combination with, software instructions for implementation of the processes of various embodiments. Thus, embodiments are not limited to any specific combination of hardware and software. A 'processor' means any one or more microprocessors, Central Processing Unit (CPU) devices, computing devices, microcontrollers, digital signal processors or like devices. The term 'computer-readable medium' refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include Dynamic Random Access Memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during Radio Frequency (RF) and Infrared (IR) data communications. Common forms of computer-readable media include, for example, a floppy disk, a flexible disk, hard disk, magnetic tape, any other magnetic medium, a Compact Disc-Read Only Memory (CD-ROM), Digital Versatile Disc (DVD), any other optical medium, punch cards, paper tape, any other physical medium with patterns of holes, a Random Access Memory (RAM), a Programmable Read Only Memory (PROM), an Erasable Programmable Read Only Memory (EPROM), an Electrically Erasable Programmable Read Only Memory (EEPROM), a flash memory, any other memory chip or cartridge, a carrier wave as described hereinafter, or any other medium from which a computer can read. In general, the computer-readable programs may be implemented in any programming language. Some examples of languages that can be used include C, C++, C#, or JAVA. The software programs may be stored on or in one or more mediums as an object code. A computer program product comprising computer executable instructions embodied in a computer-readable medium comprises computer parsable codes for the implementation of the processes of various embodiments.

Where databases are described such as the patient information database 303, the disease and case management database 306, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats including relational databases, object-based models and/or distributed databases could be used to store and manipulate the data types described herein. Likewise, object methods or behaviors of a database can be used to implement various processes, such as the described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, Local Area Network (LAN), Wide Area Network (WAN) or Ethernet, Token Ring, or via any appropriate communications means or combination of communications means. Each of the devices may comprise computers, such as those based on the Intel® processors, AMD® processors, UltraSPARC® processors, etc. that are adapted to communicate with the computer. Any number and type of machines may be in communication with the computer.

The foregoing examples have been provided merely for the purpose of explanation and are in no way to be construed as limiting of the present method and system disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A computer implemented method of disease based management of medical care provided to a patient population, comprising the steps of:

providing an online disease and case management system for the management of medical care of said disease;

providing a plurality of online information sources accessible by the online case management system, wherein said online information sources comprise information entered by a patient and an existing provider for medical treatment, wherein said online information sources include member information, provider information, medical claims, pharmacy claims, referrals and authorizations information, information from labs and images, and patient surveys;

retrieving patient information of said patient population from said plurality of online information sources by said online disease and case management system;

identifying a disease condition of the patient population from said retrieved patient information;

enrolling patients of the patient population with said disease condition for the disease based management of medical care;

assigning a disease manager to each of said enrolled patients using said online disease and case management system, wherein said disease manager manages said enrolled patient and provides personalized support for said enrolled patient;

educating said enrolled patients about the disease condition for self monitoring of the disease condition;

recording status of said self monitored disease condition in a disease log of personal health record on the online disease and case management system by the enrolled patients;

scheduling visit to a provider for medical treatment of the enrolled patients by a scheduling engine of the online disease and case management system, wherein said scheduling engine schedules said visit based on said recorded status;

synchronizing schedules of the enrolled patients with schedules of one or more of said disease manager and said provider for medical treatment;

generating a plurality of reports of the disease based management of medical care provided to the patient population, wherein said generated reports comprise utilization metrics of the disease based management of medical care, further wherein said utilization metrics are used for rewarding said provider, said disease manager, and the enrolled patients; and monitoring medical progress of the enrolled patients based on said medical treatment;

whereby the disease based management of medical care using the online disease and case management system improves quality of the medical care and reduces medical care costs.

2. The computer implemented method of claim 1, wherein the enrolled patients are managed by a disease manager, wherein said disease manager educates the enrolled patients about the disease condition.

3. The computer implemented method of claim 1, wherein said plurality of online information sources includes one or more of claim data, health risk questionnaires, and utilization analytics data.

4. The computer implemented method of claim 1, wherein said step of identifying a disease condition of the patient population is performed utilizing at least one of diagnosis codes and service codes in said medical or pharmacy claim, lab and imaging values in said lab and imaging report, clinical values in said authorization request, information provided by the patients in a health risk questionnaire, and information provided by the patients in said patient survey.

5. The computer implemented method of claim 1, wherein said step of enrolling patients of the patient population comprises inviting the patients for joining the disease based management of medical care utilizing one of electronic and non electronic communication means.

6. The computer implemented method of claim 5, wherein said invited patients are provided with user name and password for using the online disease and case management system.

7. The computer implemented method of claim 1, wherein said step of educating the enrolled patients comprises providing one or more of disease information material, instructions to the enrolled patients on general and specific medical care, and responses to queries of the enrolled patients using the online disease and case management system.

8. The computer implemented method of claim 1, wherein said step of recording status of the enrolled patients is used to determine medical status of the enrolled patients, wherein said medical status is one of acute medical status and normal medical status.

9. The computer implemented method of claim 1, wherein said step of monitoring medical progress is performed utilizing one or more of laboratory results and clinical values of the enrolled patients.

10. The computer implemented method of claim 1, further comprising a step of assessing the performance of a disease manager, a disease management supervisor, and said provider by calculating a success rate periodically, wherein said success rate is calculated from a plurality of performance indices.

11. A computer implemented method of case based management of medical care provided to a patient, comprising the steps of:

providing an online disease and case management system for said case based management of medical care;

providing a plurality of online information sources accessible by the online case management system, wherein said online information sources comprise information entered by a patient and an existing provider for medical treatment, wherein said online information sources include member information, provider information, medical claims, pharmacy claims, referrals and authorizations information, information from labs and images, and patient surveys;

retrieving information of said patient from said plurality of information sources by said online disease and case management system;

identifying a patient with a disease condition based on said retrieved patient information;

enrolling said identified patient for the case based management of medical care;

assigning a disease manager to each of said enrolled patients using said online disease and case management system, wherein said disease manager manages said enrolled patient and provides personalized support for said enrolled patient;

educating said enrolled patient about said disease condition for self monitoring of the disease condition by said disease manager;

educating the enrolled patient for one or more of support services including community programs related to the disease condition, coordination between providers of medical care, transport services, and financial counseling, wherein said disease manager accesses said online information sources and enters information about said patient and said disease condition of said patient;

recording status of said self monitored disease condition in a disease log of personal health record on the online disease and case management system by the enrolled patient;

scheduling visit to a provider for medical treatment of the enrolled patient by a scheduling engine of the online disease and case management system, wherein said scheduling engine schedules said visit based on said recorded status;

synchronizing schedules of the enrolled patients with schedules of one or more of said disease manager and said provider for medical treatment;

generating a plurality of reports of the case based management of medical care provided to the patient population, wherein said generated reports comprise utilization metrics of the disease based management of medical care, further wherein said utilization metrics are used for rewarding said provider, said disease manager, and the enrolled patients; and monitoring medical progress of the enrolled patient based on said medical treatment.

12. A computer implemented system for a disease based and a case based management of medical care provided to patients, comprising:

a computer comprising a plurality of processors for executing instructions, said computer further comprising:

an online disease and case management system for providing one of said disease and said case based management of medical care;

providing a plurality of online information sources accessible by the online case management system, wherein said online information sources comprise information entered by a patient and an existing provider for medical treatment, wherein said online information sources include member information, provider information, medical claims, pharmacy claims, referrals and authorizations information, information from labs and images, and patient surveys;

an online patient management module for coordinating one of the disease and the case based management of medical care, comprising:

a patient enrolling engine for enrolling said patients for one of the disease and the case based management of medical care;

assigning a disease manager to each of said enrolled patients using said online disease and case management system, wherein said disease manager manages said enrolled patient and provides personalized support for said enrolled patient;

an education and instruction module for providing information on self monitoring of a disease condition to the patients;

a disease log for recording status of said self monitored disease condition by the patients;

a scheduling engine for scheduling a visit to a provider for medical treatment of said enrolled patients based on said recorded status, wherein said scheduling engine synchronizes schedules of the enrolled patients with schedules of one or more of a disease manager and said provider;

a report generation tool for generating a plurality of reports of the disease based management of medical care provided to the patient population; wherein said generated reports comprise utilization metrics of the disease based management of medical care, further wherein said utilization metrics are used for rewarding said provider, said disease manager, and the enrolled patients;

a patient medical progress monitoring engine for monitoring medical progress of the enrolled patients based on said medical treatment; and a disease and case management database for storing one or more of said education and instruction information, recorded status, patient schedules, and medical progress of the enrolled patient.

13. The computer implemented system of claim 12, further comprising a patient information retrieval engine for retrieving information of the patients from a plurality of online information sources by said online disease and case management system through a communication network.

14. The computer implemented system of claim 12, further comprising a patient and disease identification module for identifying a disease condition of a patient population.

15. The computer implemented system of claim 14, wherein said patient and disease identification module is used for identifying a patient with a disease condition.

16. The computer implemented system of claim 12, further comprising a performance analysis module used for analyzing the performance of one of said provider, said disease manager, and a case manager, and providing a ranking based on said performance for the disease based and case based management of medical care of the patients.

17. The computer implemented system of claim 12, further comprising a patient information database for storing information on one or more of retrieved patient information, identified patient information, enrolled patient information, and non enrolled patient information.

18. A computer program product comprising computer executable instructions embodied in a non-transitory computer-readable medium, wherein said computer program product comprises:

a first computer parsable program code for providing an online disease and case management system for disease based and case based management of medical care;

a second computer parsable program code for retrieving information of patients from a plurality of online information sources by the online disease and case management system; wherein said online information sources include member information, provider information, medical claims, pharmacy claims, referrals and authorizations information, information from labs and images, and patient surveys;

a third computer parsable program code for identifying the disease conditions of a population and the patient with a disease condition based on the retrieved information;

a fourth computer parsable program code for enrolling the identified patients for the disease based and case based management of medical care;

a fifth computer parsable program code to assigning a disease manager for each of said enrolled patients; wherein said disease manager manages said enrolled patient and provides personalized support for said enrolled patient;

a sixth computer parsable program code for educating the enrolled patients about the disease condition for self monitoring of the disease condition;

a seventh computer parsable program code for recording status of the self monitored disease condition in a disease log of personal health record on the online disease and case management system by the patients;

an eighth computer parsable program code for scheduling visit to a provider for medical treatment of the enrolled patients based on the recorded status;

a ninth computer parsable program code for synchronizing schedules of the enrolled patients with schedules of one or more of said disease manager and said provider for medical treatment;

a tenth computer parsable program code for generating a plurality of reports of the disease based and case based management of medical care provided to the patient population, wherein said generated reports comprise utilization metrics of the disease based management of medical care, further wherein said utilization metrics are used for rewarding said provider, said disease manager, and the enrolled patients; and an eleventh computer parsable program code for monitoring medical progress of the enrolled patients based on the medical treatment.

* * * * *